United States Patent [19]

Montavon et al.

[11] 4,349,672

[45] * Sep. 14, 1982

[54] CEPHALOSPORIN DERIVATIVES

[75] Inventors: Marc Montavon; Roland Reiner, both of Basel, Switzerland

[73] Assignee: Hoffmann-La Roche Inc., Nutley, N.J.

[*] Notice: The portion of the term of this patent subsequent to Apr. 27, 1999, has been disclaimed.

[21] Appl. No.: 207,163

[22] Filed: Nov. 17, 1980

[30] Foreign Application Priority Data

Nov. 29, 1979 [CH] Switzerland .................. 10601/79

[51] Int. Cl.³ .................. C07D 501/36; A61K 31/545
[52] U.S. Cl. .................. 544/027; 424/246; 544/21
[58] Field of Search .................. 544/21, 27, 28; 424/246

[56] References Cited

U.S. PATENT DOCUMENTS

| 4,091,211 | 5/1978 | Montavon et al. | 544/27 |
| 4,144,391 | 3/1979 | Hatfield | 544/27 |
| 4,200,745 | 4/1980 | Katner | 544/21 |

*Primary Examiner*—Nicholas S. Rizzo
*Attorney, Agent, or Firm*—Jon S. Saxe; Bernard S. Leon; Frank P. Hoffman

[57] ABSTRACT

There are presented cephalosporin derivatives of the formula wherein X is the group R is hydrogen or a readily hydrolyzable ester or ether group and n stands for 1 or 2, as well as salts of these compounds and hydrates of these compounds and salts.

10 Claims, No Drawings

CEPHALOSPORIN DERIVATIVES

DESCRIPTION OF THE INVENTION

The present invention is concerned with novel cephalosporin derivatives.

The cephalosporin derivatives provided by the present invention are compounds of the formula

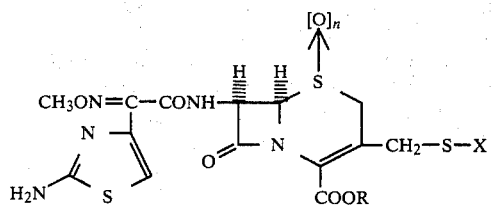
I wherein X is the group

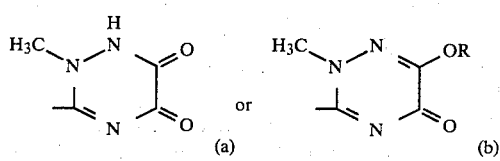

R is hydrogen or a readily hydrolysable ester or ether group and n stands for 1 or 2,
as well as salts of these compounds and hydrates of these compounds and salts.

Where R in group (b) is hydrogen, this group is present in tautomeric equilibrium with group (a).

When n in formula I stands for 1, the compounds are sulphoxides. The oxygen atom of the sulphoxide group can be either in the α-position (R configuration) or in the β-position (S configuration) or mixtures of these two configurations can be present. When n in formula I stands for 2, the compounds are sulphones (dioxides).

As readily hydrolysable ester groups denoted by R in the compounds of formula I there are to be understood R-groups on the carboxyl function which are present in the form of a readily hydrolysable ester group. Examples of such ester groups, which can be of the conventional type, are lower alkanoyloxyalkyl groups (e.g. the acetoxymethyl, pivaloyloxymentyl, 1-acetoxyethyl and 1-pivaloyloxyethyl group), lower alkoxycarbonyloxyalkyl groups (e.g. the methoxycarbonyloxymethyl, 1-ethoxycarbonyloxyethyl and 1-isopropoxycarbonyloxyethyl group), lactonyl groups (e.g. the phthalidyl and thiophthalidyl group), lower alkoxymethyl groups (e.g. the methoxymethyl group) and lower alkanoylaminomethyl groups (e.g. the acetamidomethyl group).

As readily hydrolysable ether groups denoted by R in the compounds of formula I there are to be understood R-groups on the enolic function of the 2,5-dihydro-6-hydroxy-2-methyl-5-oxo-as-triazin-3-yl group of formula (b) which are present in the form of a readily hydrolysable ether group. Such ether groups can be the same groups which have already been mentioned earlier in connection with the readily hydrolysable ester groups. Examples of such ethers are thus, for example, the lower alkanoyloxyalkyl ethers (e.g. the acetoxymethyl, pivaloyloxymethyl, 1-acetoxyethyl and 1-pivaloyloxyethyl ether), the lower alkoxycarbonyloxyalkyl ethers (e.g. the methoxycarbonyloxymethyl, 1-ethoxycarbonyloxyethyl and 1-isopropoxycarbonyloxyethyl ether), the lactonyl ethers (e.g. the phthalidyl and thiophthalidyl ether), the lower alkoxymethyl ethers (e.g. the methoxymethyl ether) and the lower alkanoylaminomethyl ethers (e.g. the acetamidomethyl ether).

Examples of salts of compounds of formula I are alkali metal salts such as the sodium and potassium salt, the ammonium salt, alkaline earth metal salts such as the calcium salt, salts with organic bases such as salts with amines (e.g. salts with N-ethyl-piperidine, procaine, dibenzylamine, N,N'-dibenzylethylethylenediamine, alkylamines or dialkylamines) and salts with amino acids (e.g. salts with arginine or lysine). The salts can be mono-salts or di-salts. The second salt formation can occur in compounds with the hydroxy moiety of the 2,5-dihydro-6-hydroxy-2-methyl-5-oxo-as-triazin-3-yl group.

The compounds of formula I also form addition salts with organic or inorganic acids. Examples of such salts are hydrohalides (e.g. hydrochlorides, hydrobromides and hydroiodides), other mineral acid salts such as sulphates, nitrates, phosphates and the like, alkylsulphonates and monoarylsulphonates such as ethanesulphonates, toluenesulphonates, benzenesulphonates and the like and other organic acid salts such as acetates, tartrates, maleates, citrates, benzoates, salicylates, ascorbates and the like.

The compounds of formula I and their salts can be hydrated. The hydration can be effected in the course of the manufacturing process or can occur gradually as a result of the hygroscopic properties of an initially anhydrous product.

The cephalosporin derivatives provided by the present invention can be present in the syn-isomeric form (Z form)

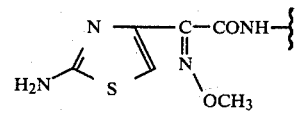

or in the anti-isomeric form (E form)

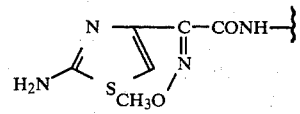

or as mixtures of these two forms, The syn-isomeric form is preferred as are mixtures in which the syn-isomeric form predominates.

Preferred cephalosporin derivatives provided by the present invention are:

(6R,7R)-7-[2-(2-amino-4-thiazolyl)-2-[(Z)-methoxyimino]-acetamido]-3-[[(2,5-dihydro-6-hydroxy-2-methyl-5-oxo-as-triazin-3-yl)thiomethyl]-8-oxo-5-thia-1-azabicyclo[4.2.0]oct-2-ene-2-carboxylic acid 5-(S)-oxide and its salts as well as the corresponding hydrates;

methylene (6R,7R)-7-[2-(2-amino-4-thiazolyl)-2-[(Z)-methoxyimino]acetamido]-3-[[(2,5-dihydro-2-methyl-5-oxo-6-[(pivaloyloxy)methoxy]-as-triazin-3-yl)thio]methyl]-8-oxo-5-thia-1-azabicyclo[4.2.0]oct-2-ene-2-carboxylate pivalate 5-(S)-oxide and its salts as well as the corresponding hydrates;

(6R,7R)-7-[2-(2-amino-4-thiazolyl)-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid 5,5-dioxide and its salts as well as the corresponding hydrates.

The cephalosporin derivatives aforesaid are manufactured in accordance with the present invention by (a) oxidising a compound of the formula

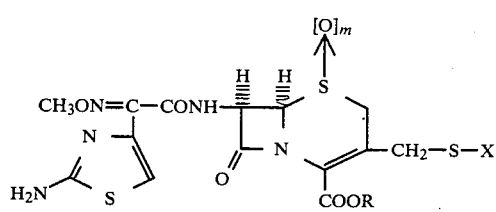

wherein X and R have the signficance given earlier and m stands for zero or 1, or a salt thereof, or (b) cleaving off the protecting group denoted by R¹ in a compound of the formula

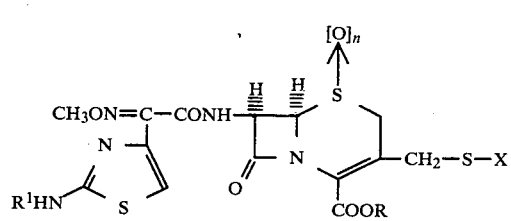

wherein X, R and n have the signficance given earlier and R¹ represents a cleavable protecting group, or in a salt thereof or (c) reacting a halide of the formula

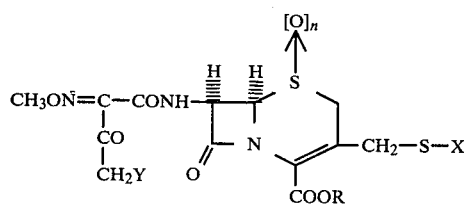

wherein X, R and n have the significance given earlier and Y represents a halogen atom, or a salt thereof, with thiourea, or (d) reacting a compound of the formula

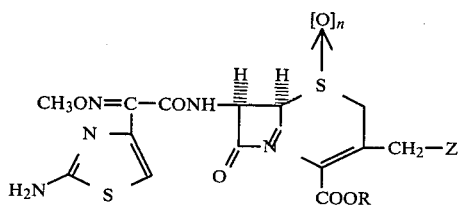

wherein R and n have the significance given earlier and Z represents a leaving group, or a salt thereof with a thiol of the formula

HS—X    VI wherein X has the significance given earlier, or (e) for the manufacture of a readily hydrolysable ester or ether of formula I, i.e. a compound of formula I in which R represents a readily hydrolysable ester or ether group, subjecting a carboxylic acid or an enol of formula I to a corresponding esterification or etherification, or (f) for the manufacture of a salt or hydrate of a compound of formula I or of a hydrate of such a salt, converting a compound of formula I into a salt or hydrate or into a hydrate of such a salt.

The starting materials of formula II in which m stands for zero, i.e. compounds which do not carry an oxygen atom on the sulphur atom of the ring, can be prepared, for example, by firstly preparing a compound of the formula

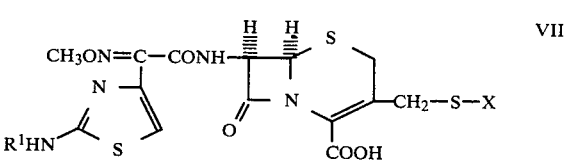

in which X and R¹ have the significance given earlier and the carboxy group can be present in protected form, by reacting a 7-amino compound of the formula

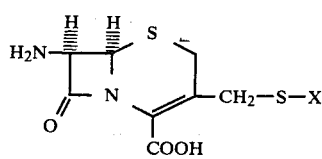

in which X has the significance given earlier and the carboxy group and/or the amino group can be present in protected form, with an acid of the formula

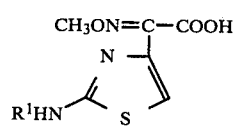

in which R¹ has the significance given earlier or with a reactive functional derivative thereof and, if desired, cleaving off a carboxy protecting group which may be present.

If desired, the carboxy group present in the compounds of formula VII can be protected; for example, by esterification to form a readily cleavable ester such as a silyl ester (e.g. the trimethylsilyl ester). The carboxy group can also be protected in the form of one of the aforementioned readily hydrolysable esters. Furthermore, the carboxy group can be protected by salt formation with an inorganic or tertiary organic base such as triethylamine. Possible protecting groups denoted by R¹ in the compounds of formulae VII and IX are, for example, protecting groups which are cleavable by acid hydrolysis (e.g. the tert.butoxycarbonyl or trityl group) or protecting groups which are cleavable by basic hydrolysis (e.g. the trifluoroacetyl group). Preferred protecting groups denoted by R¹ are the chloroacetyl, bromoacetyl and iodoacetyl groups, especially the chloroacetyl group. The last-mentioned protecting groups can be cleaved off by treatment with thiourea.

If desired, the carboxy group present in a 7-amino compound of formula VIII can also be protected in the manner mentioned earlier in connection with the compounds of formula VII to be prepared. The amino group present in a 7-amino compound of formula VIII can be protected, for example, by a silyl protecting group such as the trimethylsilyl group.

Examples of reactive functional derivatives of acids of formula IX are halides (i.e. chlorides, bromides and fluorides), azides, anhydrides, especially mixed anhydrides with strong acids, reactive esters (e.g. N-hydroxysuccinimide esters) and amides (e.g. imidazolides).

The reaction of a 7-amino compound of formula VIII with an acid of formula IX or a reactive functional derivative thereof can be carried out in a manner known per se. Thus, for example, a free acid of formula IX can be reacted with an aforementioned ester of a 7-amino compound of formula VIII in the presence of a carbodiimide such as N,N-dicyclohexylcarbodiimide in an inert solvent such as ethyl acetate, acetonitrile, dioxan, chloroform, methylene chloride, benzene or dimethylformamide and subsequently the ester group can be cleaved off. Oxazolium salts (e.g. N-ethyl-5-phenyl-isoxazolium-3'-sulphonate) can be used in place of carbodiimides in the foregoing reaction.

According to another embodiment, an acid halide, preferably the chloride, of an acid of formula IX is reacted with a 7-amino compound of formula VIII. The reaction is preferably carried out in the presence of an acid-binding agent, for example, in the presence of aqueous alkali, preferably sodium hydroxide, or in the presence of an alkali metal carbonate such as potassium carbonate or in the presence of a lower alkylamine such as triethylamine. As the solvent there is preferably used water, optionally in admixture with an inert organic solvent such as tetrahydrofuran or dioxan. The reaction can also be carried out in an aprotic organic solvent such as, for example, dimethylformamide, dimethyl sulphoxide or hexamethylphosphoric acid triamide. When a silylated compound of formula VIII is used, the reaction is carried out in anhydrous medium.

The reaction of a 7-amino compound of formula VIII with an acid of formula IX or a reactive functional derivative thereof can conveniently be carried out at a temperature between about $-40°$ C. and room temperature, for example at about $0°-10°$ C.

The compounds of formula VII can also be prepared by thiolation, namely by reacting a compound of the formula

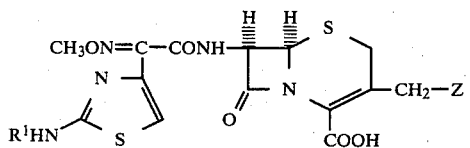

in which $R^1$ has the significance given earlier, Z is a leaving group and the carboxy group can be present in protected form, or a salt thereof, with a thiol of formula VI hereinbefore and if desired, cleaving off a carboxy protecting group which may be present.

Examples of leaving groups denoted by Z in a compound of formula X are halogen atoms (e.g. a chlorine, bromine or iodine atom), acyloxy groups (e.g. lower alkanoyloxy groups such as the acetoxy group), lower alkylsulphonyloxy or arylsulphonyloxy groups (e.g. the mesyloxy or tosyloxy group) and the azido group. The compound of formula X can be protected at the carboxy group in the same manner as described earlier in connection with the compounds of formula VII.

The reaction of a compound of formula X with a thiol of formula VI can be carried out in a manner known per se; for example, at a temperature between about $40°$ C. and $80°$ C., conveniently at about $60°$ C., in a polar solvent, for example, in an alcohol such as a lower alkanol (e.g. ethanol, n-propanol and the like), dimethylformamide or dimethyl sulphoxide, preferably in water or in a buffer solution having a pH of about 6 to 7, preferably 6.5.

An acid of formula VII obtained can be converted into a salt in the usual manner, for example, analogously to the conversion of a carboxylic acid of formula I into a salt as described hereinafter.

In order to prepare a starting material of formula II in which m stands for zero, the amino protecting group denoted by $R^1$ in an aforementioned compound of formula VII or in a salt thereof is now cleaved off. Protecting groups which are cleavable by acid hydrolysis are preferably removed with the aid of a lower alkanecarboxylic acid which may be halogenated. In particular, formic acid or trifluoroacetic acid is used. The acid hydrolysis is generally carried out at room temperature, although it can be carried out at a slightly higher or slightly lower temperature (e.g. a temperature in the range of about $0°$ C. to $+40°$ C.). Protecting groups which are cleavable under alkaline conditions are generally hydrolysed with dilute aqueous caustic alkali at $0°$ C. to $30°$ C. The chloroacetyl, bromoacetyl and iodoacetyl protecting groups can be cleaved off using thiourea in acidic, neutral or alkaline medium at about $0°-30°$ C. Hydrogenolytic cleavage (e.g. cleavage of the benzyl group) is unsuitable in this case, since the oxime function is reduced to the amino group during the hydrogenolysis.

After cleavage of the amino protecting group denoted by $R^1$, a carboxy protecting group which may be present in the product can be cleaved off if desired. When the protecting group is a silyl group (silyl ester), this group can be cleaved off especially readily by treatment with water. Lower alkanoyloxyalkyl, alkoxycarbonyloxyalkyl, lactonyl, alkoxymethyl and alkanoylaminomethyl esters are preferably cleaved enzymatically with the aid of a suitable esterase (at about $20°-40°$ C.). When the carboxy group is protected by salt formation (e.g. with triethylamine), then the cleavage of this salt-forming protecting group can be carried out by treatment with acid. Acids which can be used for this purpose are, for example, hydrochloric acid, sulphuric acid, phosphoric acid or citric acid.

An acid of formula II obtained can be converted into a salt in the usual manner, for example analogously to the conversion of a carboxylic acid of formula I into a salt as described hereinafter.

Embodiment (a) of the process provided by the present invention, i.e. the oxidation of a compound of formula II in which m stands for zero or a salt thereof, is carried out by treatment with an organic or inorganic oxidising agent. Various compounds which readily yield oxygen can be used as the oxidising agent; for example, organic peroxides such as monosubstituted organic peroxides (e.g. $C_1-C_4$ alkyl- or alkanoylhydroperoxides such as tert.butylhydroperoxide) performic acid and peracetic acid, as well as phenyl-substituted derivatives of these hydroperoxides such as cumenehydroperoxide and perbenzoic acid. The phenyl substituent can, if desired, carry a further lower group (e.g. a $C_1$-$C_4$ alkyl or alkoxy group), a halogen atom or a carboxy group (e.g. 4-methylperbenzoic acid, 4-methoxyperbenzoic acid, 3-chloroperbenzoic acid and monoperphthalic acid). Various inorganic oxidising agents can also be used as the oxidising agent; for example, hydrogen peroxide, ozone, permanganates such as potassium or sodium permanganate, hypochlorites such as sodium, potassium or ammonium hypochlorite, peroxymonosulphuric and peroxydisulphuric acid. The use of 3-chloroperbenzoic acid is preferred. The oxidation is advantageously carried out in an inert solvent, for example, in an aprotic inert solvent such as tetrahydrofuran, dioxan, methylene chloride, chloroform, ethyl acetate or acetone or in a protic solvent such as water, a lower alkanol (e.g. methanol or ethanol) or a lower alkanecarboxylic acid which may be halogenated (e.g. formic acid, acetic acid or trifluoroacetic acid). The oxidation is generally carried out at a temperature in the range of $-20°$ C. to $+50°$ C.

When the oxidising agent is used in equimolar amounts or in slight excess in relation to the starting material there is mainly obtained the corresponding sulphoxide, i.e. a compound of formula I in which n stands for 1. When the amount of oxidising agent is increased to double the stoichiometric ratio or more, there is obtained the corresponding sulphone, i.e. a compound of formula I in which n stands for 2. It is also possible to obtain the sulphone from the corresponding sulphoxide by treatment with an equimolar or greater amount of the oxidising agent. The process conditions are essentially the same as in the manufacture of the sulphoxides.

The preparation of a starting material of formula III can be carried out by oxidising an aforementioned compound of formula VII. The conditions for this oxidation are essentially the same as those described earlier in connection with the oxidation of a starting material of formula II.

An acid of formula III obtained can be converted into a salt in the usual manner, for example, analogously to the conversion of a carboxylic acid of formula I into a salt as described hereinafter.

Embodiment (b) of the process provided by the present invention, i.e. the cleavage of the amino protecting group denoted by $R^1$ in a compound of formula III or in a salt thereof, is carried out in essentially the same manner as described earlier in connection with the cleavage of the amino protecting group from a compound of formula VII.

The preparation of the starting materials of formula IV is carried out, for example, by reacting an aforementioned 7-amino compound of formula VIII with a halogenated carboxylic acid of the formula

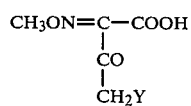

wherein Y is halogen, or with a reactive derivative thereof. The halogenated carboxylic acid of formula XI is used either in free form in the presence of a condensing agent (e.g. a N,N'-disubstituted carbodiimide such as N,N'-dicyclohexylcarbodiimide or an azolide compound such as N,N'-carbonyldiimidazole or N,N'-thionyldiimidazole) or in the form of an acid halide such as the acid chloride or bromide, in the form of an acid anhydride such as an acid anhydride with a carbonic acid monoester (e.g. with monomethyl carbonate or monoisopropyl carbonate) or in the form of an activated ester such as the p-nitrophenyl ester, 2,4-dinitrophenyl ester, N-hydroxysuccinimide ester or N-hydroxyphthalimide ester. The reaction is generally carried out in an inert organic solvent; for example, a halogenated hydrocarbon such as chloroform, dichloromethane, carbon tetrachloride, an ether such as tetrahydrofuran or dioxan, dimethylformamide, dimethylacetamide, water or mixtures thereof. The reaction is preferably carried out at a temperature in the range of about $-50°$ C. to $40°$ C., especially at about $-10°$ C. to $+10°$ C.

The foregoing reaction of a 7-amino compound of formula VIII with a halogenated carboxylic acid of formula XI or with a reactive derivative thereof gives a compound of the formula

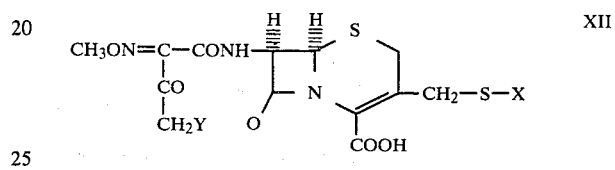

wherein X and Y have the significance given earlier and the carboxy group can be present in protected form.

The compounds of formula XII are converted by oxidation into the desired starting materials of formula IV, the oxidation conditions being essentially the same as those described earlier in connection with the oxidation of a starting material of formula II. If desired, a protecting group which may be present on the carboxy group can be cleaved off analogously to the cleavage of the carboxy protecting group described earlier in connection with the conversion of a compound of formula VII into a starting material of formula II.

An acid of formula IV obtained can be converted into a salt in the usual manner, for example, analogously to the conversion of a carboxylic acid of formula I into a salt as described hereinafter.

The reaction of a halide of formula IV or a salt thereof with thiourea in accordance with embodiment (c) of the process provided by the present invention is preferably carried out in an inert solvent such as, for example, a lower alkanol (e.g. ethanol), a lower ketone (e.g. acetone), an ether (e.g. tetrahydrofuran or dioxan), dimethylformamide, dimethylacetamide, water or mixtures thereof. The reaction is generally carried out at a temperature in the range of from about 0° C. to 60° C., preferably at room temperature. The chloride, bromine, fluoride or iodide can be used as the halide of formula IV, the chloride or bromide being preferred. The free acid of formula IV or a salt thereof can be used, optionally also salts of the acids of formula IV e.g. the same salts as those mentioned earlier in connection with the salts of the compounds of formula I.

The starting materials of formula V can be prepared by oxidising a compound of formula X in essentially the same manner as described earlier in connection with the oxidation of a starting material of formula II and cleavage of the amino protecting group denoted by $R^1$ in essentially the same manner as described earlier in connection with the cleavage of this group from a compound of formula VII.

An acid of formula V obtained can be converted into a salt in the usual manner, for example, analogously to the conversion of a carboxylic acid of formula I into a salt as described hereinafter.

Embodiment (d) of the process provided by the present invention, i.e. the thiolation of a starting material of formula V or a salt thereof with a thiol of formula VI, can be carried out in essentially the same manner as described earlier in connection with the thiolation of a compound of formula X.

In order to manufacture a readily hydrolysable ester of the carboxylic acids of formula I in accordance with embodiment (e) of the process provided by the present invention, a carboxylic acid of formula I is preferably reacted with a corresponding halide, preferably an iodide, containing the desired ester group. The reaction can be accelerated with the aid of a base such as an alkali metal hydroxide, an alkali metal carbonate or an organic amine such as triethylamine. If the 2,5-dihydro-6-hydroxy-2-methyl-5-oxo-as-triazin-3-yl group with its enolic function is present, this is etherified with the formation of a corresponding readily hydrolysable ether. In this case there is preferably used an excess of the corresponding halide. The esterification/etherification is preferably carried out in an inert organic solvent such as dimethylacetamide; hexamethylphosphoric acid triamide, dimethyl sulphoxide or, especially, dimethylformamide. The reaction is preferably carried out at a temperature in the range of about 0°–40° C.

The manufacture of the salts and hydrates of the compounds of formula I or the hydrates of said salts in accordance with embodiment (f) of the process provided by the present invention can be carried out in a manner known per se; for example, by reacting a carboxylic acid of formula I with an equivalent amount of the desired base, conveniently in a solvent such as water or an organic solvent (e.g. ethanol, methanol, acetone and the like). When a second equivalent of base is used, salt formation also takes place on a tautomeric enol form which may be present (2,5-dihydro-6-hydroxy-2-methyl-5-oxo-as-triazin-3-yl group X), whereby a di-salt is formed. The temperature at which the salt formation is carried out is not critical. The salt formation is generally carried out at room temperature, but it can be carried out at a temperature slightly above or below room temperature, for example in the range of 0° C. to +50° C.

The manufacture of the hydrates usually takes place automatically in the course of the manufacturing process or as a result of the hygroscopic properties of an initially anhydrous product. For the controlled manufacture of a hydrate, a completely or partially anhydrous carboxylic acid or formula I or ester, ether or salt thereof can be exposed to a moist atmosphere (e.g. at about +10° C. to +40° C.).

The 7-amino compounds of formula VIII hereinbefore can be prepared by reacting a compound of the formula

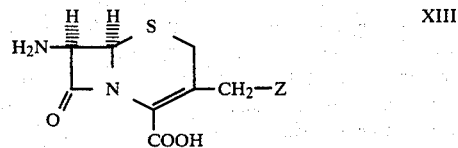

XIII wherein Z represents a leaving group and the carboxy group can be present in protected form, with a thiol of formula VI. This reaction can be carried out under the same conditions as those described earlier in connection with the reaction of a compound of formula X with a thiol of formula VI. On the other hand, a compound of formula X can be prepared from a compound of formula XIII and an acid of formula IX or a reactive functional derivative thereof under the same conditions as those described earlier in connection with the reaction of a 7-amino compound of formula VIII with an acid of formula IX or a reactive functional derivative thereof.

A syn/anti mixture of a compound of formula I which can be obtained can be separated into the corresponding syn and anti forms in the usual manner, for example by recrystallisation or by chromatographical methods using a suitable solvent or solvent mixture.

The compounds of formula I as well as the corresponding salts and the hydrates of these compounds and salts have antibiotic, especially bactericidal, activity. They possess a broad spectrum of activity against gram-positive and gram-negative microorganisms, including various β-lactamase-forming gram-negative bacteria such as, for example, Escherichia coli, Serratia marcescens, Proteus and Enterobacter species. The compounds possess particularly high β-lactamase stability.

The compounds of formula I as well as the corresponding salts and the hydrates of these compounds and salts can be used for the treatment and prophylaxis of infectious diseases. A daily dosage of about 0.1 g to about 2 g is envisaged for adults. The parenteral administration of the compounds provided by the present invention is especially preferred.

In order to demonstrate the antimicrobial activity of the cephalosporin derivatives provided by the present invention, the following representatives were tested:

Derivative A: The disodium salt of (6R,7R)-7-[2-(2-amino-4-thiazolyl)-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid 5-(s)-oxide.

Derivative B: The disodium salt of (6R,7R)-7-[2-(2-amino-4-thiazolyl)-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid 5,5-dioxide.

| Activity in vitro: Minimum inhibitory concentration (μg/ml) | | | |
| --- | --- | --- | --- |
| Causative organism | | A | B |
| GRAM POSITIVE | | | |
| Streptococcus pyogenes | | 1.6 | 3.1 |
| GRAM NEGATIVE | | | |
| Escherichia coli | Strain 1 | 0.025 | 0.05 |
| | Strain 2 | 0.19 | 0.39 |
| | Strain 3 | 0.10 | 0.19 |
| | Strain 4 | 0.10 | 0.39 |
| Enterobacter cloacae | Strain 1 | 3.1 | 6.3 |
| | Strain 2 | 0.19 | 0.39 |
| Enterobacter aerogenes | Strain 1 | 0.19 | 0.39 |
| | Strain 2 | 0.10 | 0.10 |
| Klebsiella pneumoniae | Strain 1 | 0.10 | 0.39 |
| | Strain 2 | 0.025 | 0.19 |
| | Strain 3 | 0.10 | 0.19 |
| Citrobacter freundii | Strain 1 | 0.19 | 0.19 |
| | Strain 2 | 0.05 | 0.19 |
| Acinetobacter anitratus | | 25 | 100 |
| Proteus mirabilis | Strain 1 | 0.025 | 0.10 |
| | Strain 2 | 0.39 | 0.78 |
| Proteus inconstans | | ≦0.006 | 0.025 |
| Proteus vulgaris | Strain 1 | 0.10 | 0.39 |
| | Strain 2 | 0.10 | 0.19 |
| | Strain 3 | 0.05 | 0.19 |
| Proteus rettgeri | | ≦0.006 | 0.05 |
| Serratia marcescens | Strain 1 | 0.39 | 1.6 |

| Activity in vitro: Minimum inhibitory concentration (μg/ml) | | |
|---|---|---|
| Causative organism | A | B |
| Strain 2 | 0.19 | 0.78 |

The cephalosporin derivatives provided by the present invention can be used as medicaments; for example, in the form of pharmaceutical preparations which contain them in association with a compatible pharmaceutical carrier material. This carrier material can be an organic or inorganic inert carrier material which is suitable for enteral or parenteral administration such as, for example, water, gelatin, gum arabic, lactose, starch, magnesium stearate, talc, vegetable oils, polyalkyleneglycols, petroleum jelly etc. The pharmaceutical preparations can be made up in solid form (e.g. as tablets, dragees, suppositories or capsules) or in liquid form (e.g. as solutions, suspensions or emulsions). The pharmaceutical preparations may be sterilised and/or may contain adjuvants such as preserving, stabilising, wetting or emulsifying agents, salts for varying the osmotic pressure, anaesthetics or buffers. The pharmaceutical preparations can also contain other therapeutically valuable substances. The compounds of formula I in which R represents a hydrogen atom as well as their salts and hydrates are especially suitable for parenteral administration and for this purpose they are preferably made up in the form of lyophilisates or dry powders for dilution with customary agents such as water or isotonic sodium chloride solution. The readily hydrolysable esters or ethers of formula I as well as their salts and hydrates are also suitable for enteral administration.

The following Examples illustrate the process provided by the present invention:

EXAMPLE 1

Manufacture of the disodium salt of (6R,7R)-7-[2-(2-amino-4-thiazolyl)-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid 5-(S)-oxide.

5 g of the disodium salt of (6R,7R)-7-[2-(2-amino-4-thiazolyl)-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid are dissolved in 100 ml of water. A solution of 1.85 g of 3-chloroperbenzoic acid (85%) in 50 ml of ethanol is added dropwise to this solution during 0.5 hour, the temperature being held at 25°–28° C. The mixture is then stirred at 25° C. for 1 hour and subsequently concentrated in vacuo. The resulting suspension is partitioned between water and ethyl acetate. The aqueous solution is washed once with ethyl acetate and evaporated at 50° C. in vacuo. The residue is dissolved in 50 ml of water and, while stirring, treated slowly with acetone until turbidity begins. The crystallisation of the title substance is induced by scratching with a glass rod. After stirring for 30 minutes, the crystallisate is filtered off under suction and washed successively with 100 ml of acetone/water (8:2), 100 ml of acetone and 100 ml of low-boiling petroleum ether. There is obtained pure title substance as almost colourless crystals with $[\alpha]_D^{25} = -117°$ (c=1 in water). $^1$H-NMR spectrum in $D_2O$ (δ-values in ppm, s=singlet, d=doublet, q=quartet; J=coupling constants in Hz, number of protons in parentheses): 3.65 (N—CH$_3$) (s) (3), 3.87 (2—CH$_2$) (AB-q/centering value; $J_{gem}$=18 Hz) (2),

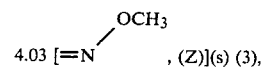
4.03 [=N$^{OCH_3}$ , (Z)](s) (3), 4.29 (3—CH$_2$—S) (AB-q/centering value; $J_{gem}$=13 Hz) (2), 5.00 (H-6) (d,$J_{H\text{-}6,H\text{-}7}$=4.5 Hz) (1), 6.00 (H-7) (d,$J_{H\text{-}7,H\text{-}6}$=4.5 Hz) (1), 7.02 (thiazolyl-H) (s) (1).

The disodium salt of (6R,7R)-7-[2-(2-amino-4-thiazolyl)-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid used as the starting material can be prepared as follows:

22.24 g of 2-(2-chloroacetamido-thiazol-4-yl)-2-[(Z)-methoxyimino]acetic acid are suspended in 240 ml of methylene chloride. 13.39 ml of triethylamine are added to this suspension, a light brown solution resulting. This solution is cooled to 0°–5° C. and treated with 16.72 g of phosphorus pentachloride. The mixture is stirred at 0°–5° C. for 5 minutes and without cooling for 20 minutes. The yellow solution is evaporated at 35° C. in vacuo. The evaporation residue is shaken twice with n-heptane and the latter is decanted off. The resinous residue is treated with 240 ml of tetrahydrofuran and the insoluble triethylamine hydrochloride is filtered off. The yellow filtrate contains the acid chloride.

22 g of (7R)-7-amino-3-desacetoxy-3-[(2,5-dihydro-6-hydroxy-2-methyl-5-oxo-as-triazin-3-yl)-thio]-cephalosporanic acid are suspended in a mixture of 300 ml of water and 150 ml of tetrahydrofuran. 2 N sodium hydroxide is added dropwise to the suspension with good nitrogen gasification using an autotitrator until a brown-red solution of pH 8 results. This solution is cooled to 0°–5° C. and treated dropwise during 15 minutes with the solution of the acid chloride in tetrahydrofuran prepared as described earlier. Thereafter, the mixture is stirred at 25° C. for 2.5 hours. The pH of the acylation mixture is held constant at 8 by the addition of 2 N sodium hydroxide. The almost black solution is freed from tetrahydrofuran at 40° C. in vacuo. 100 ml of 2 N sulphuric acid are now added. The substance which thereby separates is filtered off under suction, washed with water and suction filtered well. The moist brown material on the suction filter is dissolved in 1.5 liters of acetone. The dark solution is filtered off over Hyflo from a small amount of dark insoluble material, treated with carbon, stirred for 30 minutes and again filtered over Hyflo. The orange-red filtrate is dried over sodium sulphate, concentrated in vacuo and evaporated with ethyl acetate. In so doing there separates a black resin which is filtered off and discarded. The two-phase filtrate, which still contains water, is azeotropically distilled three times with benzene at 40° in vacuo. The substance which thereby separates is filtered off under suction, dried at 40° C. in vacuo and then stirred twice with 1 liter of acetone each time, there remaining behind a brown resin which is discarded. The combined orange coloured acetone extracts are concentrated to ca 150 ml at 40° C. in vacuo, a brown resin being filtered off and discarded. The filtrate is treated with 1 liter of ethyl acetate and concentrated at 40° C. in vacuo. The substance which thereby separates is filtered off under suction, washed with ethyl acetate and thereafter with ether; there being obtained (6R,7R)-7-[2-[2-(2-chloroa cetamido)-4-thiazolyl]-2-[(Z)-methox-yimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid, Fraction I, a beige amorphous acid. This Fraction I can be used directly for the preparation of the desired starting material.

The ethyl acetate mother liquor is concentrated strongly at 40° in vacuo, diluted with ether and the separated substance is filtered off under suction; there being obtained (6R,7R)-7-[2-[2-(2-chloroacetamido)-4-thiazolyl]-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid, Fraction II, a light beige amorphous acid, which is somewhat purer that Fraction I according to thin-layer chromatography.

For the manufacture of the disodium salt, 3.5 g of acid (Fraction II) are dissolved in a mixture of 20 ml of acetone and 11 ml of water. The solution is treated with 7 ml of a 2 N solution of 2-ethylcaproic acid sodium salt in ethyl acetate, the disodium salt crystallising out. A further 25 ml of acetone are now added portionwise and the mixture is stored in a deep-freeze for 2 hours. The crystallisate is filtered off under suction, washed successively with 250 ml of ice-cold acetone/water (80:20), pure acetone and low-boiling petroleum ether and dried at 40° C. overnight in a high vacuum. There is obtained the disodium salt of (6R,7R)-7-[2-[2-(2-chloroacetamido)-4-thiazolyl]-2-[(Z)-methoxyimino]acetamido]-3-[[(2,5-dihydro-6-hydroxy-2-methyl-5-oxo-as-triazin-3-yl)thio]-methyl]-8-oxo-5-thia-1-azabicyclo[4.2.0]oct-2-ene-2-carboxylic acid in the form of light yellow crystals; $[\alpha]_D^{20} = -142.7°$ (c = 1 in water). The nuclear magnetic resonance spectrum and the microanalysis correspond to the given structure.

15.3 g of (6R,7R)-7-[2-[2-(2-chloroacetamido)-4-thiazolyl]-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid (Fraction I) are suspended in 150 ml of water together with 5 g of thiourea. While gassing well with nitrogen and stirring, the pH is adjusted to 6.8–7.0 with saturated sodium hydrogen carbonate solution, an orange coloured solution resulting. The pH of the solution is held constant at 6.8 for 6 hours by means of an autotitrator with the addition of sodium hydrogen carbonate solution. A further 2.5 g of thiourea are added and the solution is stirred for a further 3 hours, the pH being held at 6.8 with the addition of saturated sodium hydrogen carbonate solution. The red solution is stored overnight in a refrigerator, the solution becoming darker. The pH of the solution is adjusted to 2.0–2.5 by the addition of 100% formic acid, a substance separating. This substance is filtered off under suction and washed with 100 ml of 10% aqueous formic acid. The mother liquor is discarded. The brownish material on the suction filter is suspended in 200 ml of water and the pH is adjusted to 7 with triethylamine, a brown solution resulting. This solution is stirred with 2 g of active carbon for 30 minutes, the carbon is filtered off and the still brown filtrate is adjusted to pH 3.5 with 100% formic acid while stirring well. The substance which thereby separates is filtered off under suction, washed with 50 ml of 10% aqueous formic acid and discarded. The dark yellow filtrate is adjusted to pH 2–2.5 with 100% formic acid, a substance separating. This substance is filtered off under suction, washed with ice/water and dried. The cephalosporanic acid obtained is converted into the disodium salt by suspension in a mixture of 40 ml of acetone and 40 ml of water and treatment with 20 ml of a 2 N solution of 2-ethylcaproic acid sodium salt in ethyl acetate. To the thereby resulting orange coloured solution are added 50 ml of acetone, there separating a brown resin which is filtered off. The yellow filtrate is stirred for 30 minutes, the disodium salt crystallising. The mixture is treated portionwise with a further 50 ml of acetone and stored overnight in a refrigerator. The crystallisate is filtered off under suction, washed successively with acetone/water (85:15), pure acetone and low-boiling petroleum ether and dried at 40° C. overnight in vacuo. There is obtained the disodium salt of (6R,7R)-7-[2-(2-amino-4-thiazolyl)-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid in the form of beige coloured crystals; $[\alpha]_D^{20} = -144°$ (c = 0.5 in water). The nuclear magnetic resonance spectrum and the microanalysis correspond to the given structure.

EXAMPLE 2

Manufacture of methylene (6R,7R)-7-[2-(2-amino-4-thiazolyl)-2-[(Z)-methoxyimino]acetamido]-3-[[2,5-dihydro-2-methyl-5-oxo-6-[(pivaloyloxy)methoxy]-as-triazin-3-yl)thio]methyl]-8-oxo-5-thia-1-azabicyclo[4.2.0]oct-2-ene-2-carboxylate pivalate 5-(S)-oxide 0.875 g of methylene (6R,7R)-7-[2-(2-chloroacetamido-4-thiazolyl)-2-[(Z)-methoxyimino]acetamido]-3-[[(2,5-dihydro-2-methyl-5-oxo-6-[(pivaloyloxy)methoxy]-as-triazin-3-yl)thio]methyl]-8-oxo-5-thia-1-azabicyclo[4.2.0]oct-2-ene-2-carboxylate pivalate 5-(S)-oxide is dissolved in 15 ml of N,N-dimethylacetamide together with 0.500 g of thiourea. The solution is stirred at 25° C. for 2 hours and subsequently poured into 200 ml of ethyl acetate. The mixture is washed once with 5% aqueous sodium hydrogen carbonate solution and twice with water. The organic phase is dried over sodium sulphate and evaporated at 40° C. in vacuo. For purification, the brownish residue is chromatographed on a silica gel column with benzene/ethanol (9:1) and benzene/ethanol (8:2). The fractions containing the title substance are combined and concentrated strongly at 40° C. in vacuo. The concentrate is treated with ether, the light beige title substance separating in amorphous form. $^1$H-NMR spectrum in DMSO-d$_6$ (δ-values in ppm, s=singlet, d=doublet, q=quartet, m=multiplet, b=broad, J=coupling constants in Hz; number of protons in parentheses): 1.18 [2×C—(CH$_3$)$_3$](s)(18), 3.68 (N—CH$_3$)(s) (3),

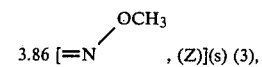

3.86 [=N—OCH$_3$, (Z)](s) (3), 4.45 (3—CH$_2$—S)(AB-q/centering value; $J_{gem}$=14 Hz)(2), 4.96 (H-6)(d, $J_{H-6,H-7}$=5 Hz)(1), 5.85 (2×O—CH$_2$—O)(m)(4), 6.03 (H-7)(q, $J_{H-7,HN}$=8 Hz, $J_{H-7,H-6}$=5 Hz)(1), 6.82 (thiazolyl-H)(s)(1), 7.17 (—NH$_2$) (b)(2), 8.77 (7—NH) (d,$J_{NH,H-7}$=8 Hz)(1).

The methylene (6R,7R)-7-[2-(2-chloroacetamido-4-thiazolyl)-2-[(Z)-methoxyimino]acetamido]-3-[[(2,5-dihydro-2-methyl-5-oxo-6-[(pivaloyloxy)methoxy]-as-triazin-3-yl)thio]methyl]-8-oxo-5-thia-1-azabicyclo[4.2.-

0]oct-2-ene-2-carboxylate pivalate 5-(S)-oxide used as the starting material can be prepared as follows:

13.5 g of the disodium salt of (6R,7R)-7-[2-(2-chloroacetamido-4-thiazolyl)-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid are suspended in 400 ml of dimethylformamide. The suspension is cooled to 0°–5° C., stirred for 15 minutes and treated with 8.8 g of pivaloyloxymethyl iodide. The mixture is stirred at 0°–5° C. for 30 minutes, subsequently poured into 2 liters of ethyl acetate and washed successively with 400 ml of water, twice with 600 ml of 1 M aqueous sodium hydrogen carbonate solution each time and twice with 1 liter of water each time. The organic phase is dried over sodium sulphate and concentrated to a volume of ca 50 ml at 40° C. in vacuo. This concentrate is treated with ether while stirring, the crude product separating. After precipitation from ethyl acetate/ether and drying at 25° C. overnight in vacuo, there is obtained a preliminarily purified product which, for further purification, is chromatographed on a silica gel column using ethyl acetate for the elution. The fractions containing the product are combined and evaporated. The residue is crystallised from ethyl acetate/ether and yields pure, beige methylene (6R,7R)-7-[2-(2-chloroacetamido-4-thiazolyl)-2-[(Z)-methoxyimino]acetamido]-3-[[(2,5-dihydro-2-methyl-5-oxo-6-[(pivaloyloxy)methoxy]-as-triazin-3-yl)thio]methyl]-8-oxo-5-thia-1-azabicyclo[4.2.0]oct-2-ene-2-carboxylate pivalate; $[\alpha]_D^{25} = -202.7°$ (c=0.7837 in acetone).

$^1$H-NMR spectrum in DMSO-d$_6$ (δ-values in ppm, s=singlet, d=doublet, q=quartet, m=multiplet, J=coupling constants in Hz, number of protons in parentheses): 1.15 [2×C(CH$_3$)$_3$](s)(18). 3.61 (N—CH$_3$)(s)(3), ca 3.66 (2—CH$_2$)(AB-q/centering value; $J_{gem}$=ca. 12 Hz)(2),

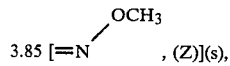

(3) 4.25 (3—CH$_2$—S)(AB-q/centering value, $J_{gem}$=14 Hz), 4.34 (Cl—CH$_2$—CO)(s)(2), 5.15 (H-6)(d, $J_{H-6,H-7}$=4.5 Hz)(1), 5.81 (2×O—CH$_2$—O) (m)(4), 5.95 (H-7)(q,$J_{H-7,NH}$=8.5 Hz), $J_{H-7,H-6}$=4.5 Hz)(1), 7.39 (thiazolyl—H)(s)(1), 9.59 (7-NH)(d, $J_{NH,H-7}$=8.5 Hz)(1), 12.81 (NH—COCH$_2$Cl)(s)(1).

5.5 g of methylene (6R,7R)-7-[2-(2-chloroacetamido-4-thiazolyl)-2-[(Z)-methoxyimino]acetamido]-3-[[(2,5-dihydro-2-methyl-5-oxo-6-[(pivaloyloxy)methoxy]-as-triazin-3-yl)thio]methyl]-8-oxo-5-thia-1-azabicyclo[4.2.0]oct-2-ene-2-carboxylate pivalate are dissolved in 25 ml of chloroform. To the solution, cooled to 0° C., is added dropwise during 20 minutes a solution of 1.34 g of 3-chloroperbenzoic acid (85%) in 20 ml of chloroform, the temperature of the solution being held between 3° C. and 5° C. The solution is then stirred at 5° C. for 15 minutes and subsequently diluted with 500 ml of ethyl acetate. After washing with aqueous sodium hydrogen carbonate solution and with water, the organic phase is evaporated at 40° C. in vacuo. The residue is a brown powder which, for purification, is chromatographed on a silica gel column using ethyl acetate/methanol (9:1) for the elution. The fractions containing the product are combined and evaporated at 40° C. in vacuo. The residue is dissolved in a small amount of ethyl acetate and precipitated by treatment with ether. The amorphous precipitate is filtered off under suction and washed successively with ether and low-boiling petroleum ether. There is obtained pure methylene (6R,7R)-7-[2-(2-chloroacetamido-4-thiazolyl)-2-[(Z)-methoxyimino]acetamido]-3-[[(2,5-dihydro-2-methyl-5-oxo-6-[(pivaloyloxy)methoxy]-as-triazin-3-yl)thio]methyl]-8-oxo-5-thia-1-azabicyclo[4.2.0]oct-2-ene-2-carboxylate pivalate 5-(S)-oxide in the form of an almost colourless powder. $^1$H-NMR spectrum in DMSO-d$_6$ (δ-values in ppm, s=singlet, d=doublet, q=quartet, J=coupling constants in Hz; number of protons in parentheses): 1.19 [2×C(CH$_3$)$_3$] (s)(18) 3.66 (N—CH$_3$)(s)(3), ca. 3.70 (2—CH$_2$)(AB-q/centering value; $J_{gem}$=ca 18 Hz)(2), $$3.93\ [=N\diagup^{OCH_3},\ (Z)](s)\ (3),$$

4.37 (Cl—CH$_2$—CO)(s)(2), ca 4.50 (3—CH$_2$—S)(AB-q/centering value; $J_{gem}$=15 Hz)(2), 5.00 (H-6)(d,$J_{H-6,H-7}$=4.5 Hz)(1), 5.87 (2×O—CH$_2$—O)(s, broad) (4), 6.07 (H-7)(q,$J_{H-7,NH}$=7.5 Hz, $J_{H-7,H-6}$=4.5 Hz)(1), 7.50 (thiazolyl—H)(s)(1), 9.03 (7-NH) (d, $J_{NH,H-7}$=7.5 Hz)(1), 12.98 (NH—COCH$_2$Cl)(s)(1).

EXAMPLE 3

Manufacture of the disodium salt of (6R,7R)-7-[2-(2-amino-4-thiazolyl)-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid 5,5-dioxide.

1.8 g of the disodium salt of (6R,7R)-7-[2-(2-amino-4-thiazolyl)-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid 5-(S)-oxide are dissolved in 35 ml of water. To this solution is added dropwise during 20 minutes a solution of 0.627 g of 3-chloroperbenzoic acid (85%) in 17 ml of ethanol, the temperature being held at 25°–28° C. (The consumption of oxidising agent is followed by potassium iodide/starch paper). The mixture is then stirred at 25° C. for 90 minutes and subsequently concentrated at 45° C. in vacuo. The concentrate is partitioned between water and ethyl acetate. The aqueous phase is washed once with ethyl acetate and evaporated at 45° C. vacuo. The residue remaining yields, after pulverisation and drying, beige-yellow title compound. $^1$H-NMR spectrum in D$_2$O (δ-values in ppm, s=singlet, d=doublet, b=broad, number of protons in parentheses): 3.71 (N—CH$_3$)(s,b)(3), $$4.02\ [=N\diagup^{OCH_3},\ (Z)](s)\ (3),$$

4.99 (H-6) (d,b)(1), 6.01 (H-7)(d,b)(1), 7.03 (thiazolyl-H)(s)(1).

The following Examples illustrate pharmaceutical preparations containing the cephalosporin derivatives provided by the present invention:

EXAMPLE A

Production of dry ampoules for intramuscular administration

A lyophilisate of 1 g of the disodium salt of (6R,7R)-7-[2-(2-amino-4-thiazolyl)-2-[(Z)-methox yimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid 5-(S)-oxide is prepared in the usual manner and filled into an ampoule. Prior to the administration, the lyophilisate is treated with 2.5 ml of a 2% aqueous lidocaine hydrochloride solution.

EXAMPLE B

An interlocking gelatin capsule containing the following ingredients is produced in the usual manner:

| | |
|---|---:|
| Methylene (6R,7R)-7-[2-(2-amino-4-thiazolyl)-2-[(Z)-methoxyimino]acetamido]-3-[[(2,5-dihydro-2-methyl-5-oxo-6-[(pivaloyloxy)-methoxy]-as-triazin-3-yl)thio]methyl]-8-oxo-5-thia-1-azabicyclo[4.2.0]oct-2-ene-carboxylate pivalate 5-(S)-oxide | 500 mg |
| Luviskol (water-soluble polyvinylpyrrolidone) | 20 mg |
| Mannitol | 20 mg |
| Talc | 15 mg |
| Magnesium stearate | 2 mg |
| | 557 mg |

What is claimed:
1. A compound of the formula

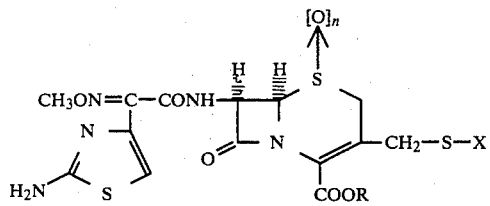

wherein X is the group

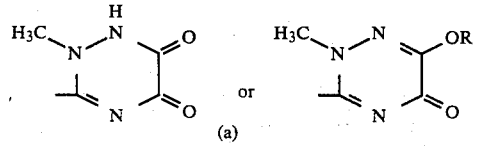

R is hydrogen or a pharmaceutically acceptable readily hydrolysable ester or ether group and n stands for 1 or 2,
the pharmaceutically acceptable salts of these compounds and the hydrates of these compounds and pharmaceutically acceptable salts.

2. The cephalosporin derivative of claim 1, wherein R is hydrogen.

3. The cephalosporin derivative of claim 1 or claim 2, wherein n stands for 1.

4. The cephalosporin derivative of claim 3, wherein the oxygen atom of the sulphoxide group is present in the β-position (S-configuration).

5. The compound: (6R,7R)-7-[2-(2-Amino-4-thiazolyl)-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid 5-(S)-oxide as well as the pharmaceutically acceptable salts of this compound and hydrates of this compound and salts.

6. The compound: (6R,7R)-7-[2-(2-Amino-4-thiazolyl)-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid 5,5-dioxide as well as the pharmaceutically acceptable salts of this compound and hydrates of this compound and salts.

7. The compound: Methylene (6R,7R)-7-[2-(2-amino-4-thiazolyl)-2-[(Z)-methoxyimino]acetamido]-3-[[(2,5-dihydro-2-methyl-5-oxo-6-[(pivaloyloxy)methoxy]-as-triazin-3-yl)thio]methyl]-8-oxo-5-thia-1-azabicyclo[4.2.0]oct-2-ene-2-carboxylate pivalate 5-(S)-oxide as well as the pharmaceutically acceptable salts of this compound and hydrates of this compound and salts.

8. A compound of the formula

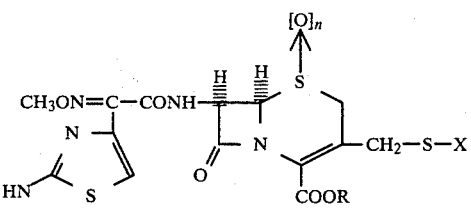

wherein X is the group

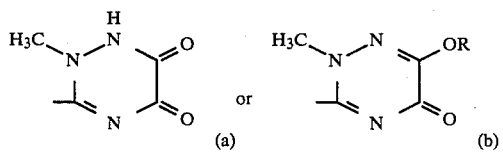

$R^1$ is a cleavable protecting group, R is hydrogen or a pharmaceutically acceptable readily hydrolysable ester or ether group and n stands for 1 or 2,
as well as the pharmaceutically acceptable salts of these compounds.

9. A compound of the formula

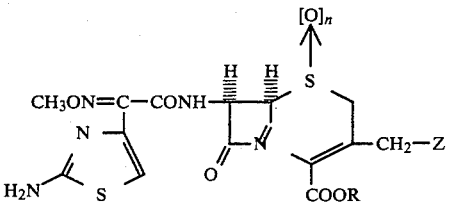

Z is a leaving group, R is hydrogen or a pharmaceutically acceptable readily hydrolysable ester or ether group and n stands for 1 or 2,
as well as the pharmaceutically acceptable salts of these compounds.

10. The compound: (6R,7)-7-[2-(2-Amino-4-thiazolyl)-2-[(Z)-methoxyimino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid 5-(S-oxide as well as the pharmaceutically acceptable salts of this compound and hydrates of this compound and salts.

* * * * *